(12) United States Patent
Saleh

(10) Patent No.: US 10,106,596 B2
(45) Date of Patent: Oct. 23, 2018

(54) FIBROUS PROTEIN PROCESSING METHOD

(75) Inventor: Mirshahin Seyed Saleh, Christchurch (NZ)

(73) Assignee: FARMCORP WOOLS LIMITED, Russley, Christchurch (NZ)

( * ) Notice: Subject to any disclaimer, the term of this patent is extended or adjusted under 35 U.S.C. 154(b) by 778 days.

(21) Appl. No.: 14/239,460

(22) PCT Filed: Aug. 17, 2012

(86) PCT No.: PCT/NZ2012/000146
§ 371 (c)(1),
(2), (4) Date: May 22, 2014

(87) PCT Pub. No.: WO2013/043062
PCT Pub. Date: Mar. 28, 2013

(65) Prior Publication Data
US 2014/0326165 A1    Nov. 6, 2014

(30) Foreign Application Priority Data

Aug. 19, 2011 (AU) ................................ 2011903326

(51) Int. Cl.
| | |
|---|---|
| C07K 14/78 | (2006.01) |
| C08H 1/06 | (2006.01) |
| C08L 89/04 | (2006.01) |
| C08L 89/00 | (2006.01) |
| C08J 5/18 | (2006.01) |
| D01D 5/06 | (2006.01) |
| D01F 4/00 | (2006.01) |
| D01F 2/08 | (2006.01) |
| D01F 6/56 | (2006.01) |

(52) U.S. Cl.
CPC .............. *C07K 14/78* (2013.01); *C08H 1/06* (2013.01); *C08J 5/18* (2013.01); *C08L 89/00* (2013.01); *C08L 89/04* (2013.01); *D01D 5/06* (2013.01); *D01F 4/00* (2013.01); *C08J 2389/00* (2013.01); *C08L 2203/12* (2013.01); *D01F 2/08* (2013.01); *D01F 6/56* (2013.01)

(58) Field of Classification Search
CPC ........... C07K 14/78; C08H 1/06; C08L 89/00; C08L 89/04; C08J 5/18; D01D 5/06; D01F 4/00
See application file for complete search history.

(56) References Cited

U.S. PATENT DOCUMENTS

| | | | | |
|---|---|---|---|---|
| 2,158,499 | A | * | 5/1939 | Grassmann ...... C07K 14/43577 435/212 |
| 2,436,156 | A | * | 2/1948 | Upson ....................... D01F 4/00 264/202 |
| 2,992,933 | A | | 7/1961 | Besso et al. |
| 6,066,316 | A | * | 5/2000 | Shiojima ................ A61K 8/044 424/401 |
| 6,221,486 | B1 | * | 4/2001 | Soane ......................... C08J 9/04 428/364 |
| 2006/0282958 | A1 | * | 12/2006 | Yang ........................ D01F 4/00 8/116.1 |
| 2007/0207111 | A1 | | 9/2007 | Nomura et al. |
| 2009/0166919 | A1 | | 7/2009 | Yamada et al. |

FOREIGN PATENT DOCUMENTS

| | | |
|---|---|---|
| EP | 628573 A1 | 12/1994 |
| EP | 0476557 B1 | 7/1995 |
| WO | 03018673 A1 | 3/2003 |
| WO | 2005028560 A1 | 3/2005 |

OTHER PUBLICATIONS

Int'l Search Report dated Feb. 15, 2013 in Int'l Application No. PCT/NZ2012/000146.
Written Opinion dated Feb. 15, 2013 in Int'l Application No. PCT/NZ2012/000146.
Written Opinion dated Aug. 7, 2013 in Int'l Application No. PCT/NZ2012/000146.
Int'l Preliminary Report on Patentability dated Oct. 30, 2013 in Int'l Application No. PCT/NZ2012/000146.
Extended Search Report dated Mar. 27, 2015 in EP Application No. 12834202.9.
Xu et al, "Dissolution and regeneration of wool via controlled disintegration and disentanglement of highly crosslinked keratin," J. Mater. Sci., vol. 49, pp. 7513-7521 (2014).
Sah et al, "Regenerated Silk Fibroin from B. mori Silk Cocoon for Tissue Engineering Applications," International Journal of Environmental Science and Development, vol. 1, No. 5, pp. 404-408 (2010).
Office Action dated Nov. 19, 2014 in NZ Application No. 622388.
Office Action dated Jun. 12, 2015 in AU Application No. 2012310322.

* cited by examiner

*Primary Examiner* — Amina S Khan
(74) *Attorney, Agent, or Firm* — Panitch Schwarze Belisario & Nadel LLP

(57) ABSTRACT

Disclosed is a process for preparing proteinaceous materials. The process comprises solubilizing fibrous protein by contacting it with an alkaline solution, ageing the resulting mixture to form a homogenous solution, and coagulating the resulting solution to form the proteinaceous material. The proteinaceous materials may be produced as, for example, fibers, films, sheets, coatings, particles, shapes, foams or composites.

18 Claims, No Drawings

FIBROUS PROTEIN PROCESSING METHOD

CROSS-REFERENCE TO RELATED APPLICATION

This application is a Section 371 of International Application No. PCT/NZ2012/000146, filed Aug. 17, 2012, which was published in the English language on Mar. 28, 2013, under International Publication No. WO 2013/043062 A1, and the disclosure of which is incorporated herein by reference in its entirety.

FIELD OF THE INVENTION

The present invention relates to a process for solubilising fibrous protein and coagulating the resulting solution to form a proteinaceous material.

BACKGROUND

Fibrous proteins (also known as scleroproteins) are generally inert and insoluble in water. Fibrous proteins form long protein filaments shaped like rods or wires. They are structural or storage proteins. Fibrous proteins include keratin, collagen, elastin and fibroin.

Wool is a keratin protein fibre and is produced by various animals including sheep, goats, camels and rabbits. The fibre structure comprises a cuticle, cortex, and medulla, although fine wools may lack the medulla.

Wool can be readily dissolved in strong alkali solutions. Treating wool with a solution of hot concentrated sodium hydroxide results in complete hydrolysis of the disulfide and peptide bonds, and the wool is eventually broken down into its constituent amino acids.

The diameter of sheep wool typically ranges from about 10 microns to about 45 microns. Fibre diameter is an important characteristic of wool in relation to its quality and price. Finer wools are softer and suitable for use in garment manufacturing. There are a limited number of consumer applications remaining for stronger wool types such as flooring, bedding, upholstery, and hand knitting yarns.

Previous attempts to reprocess coarse wool to fine wool have largely failed because of the cost of the solubilisation step.

Accordingly, it is an object of the present invention to go some way to avoiding the above disadvantages; and/or to at least provide the public with a useful choice.

Other objects of the invention may become apparent from the following description which is given by way of example only.

SUMMARY OF THE INVENTION

In a first aspect, the present invention provides a process for preparing a proteinaceous material comprising:
(a) contacting fibrous protein with an alkaline solution;
(b) optionally removing excess alkaline solution from the fibrous protein;
(c) ageing the mixture of fibrous protein and alkaline solution to form a homogenous solution; and
(d) coagulating the solution obtained in (c) to form the proteinaceous material.

In one embodiment, the present invention provides a process for preparing a proteinaceous material comprising:
contacting fibrous protein with an alkaline solution;
removing excess alkaline solution from the fibrous protein;
ageing the mixture of fibrous protein and alkaline solution to form a homogenous solution; and
coagulating the homogenous solution to form the proteinaceous material.

In another embodiment, the present invention provides a process for preparing a proteinaceous material comprising:
contacting fibrous protein with an alkaline solution;
ageing the mixture of fibrous protein and alkaline solution to form a homogenous solution; and
coagulating the homogenous solution to form the proteinaceous material.

In a second aspect, the present invention provides a proteinaceous material when prepared by a process of the first aspect.

In a third aspect, the present invention provides a proteinaceous material prepared by a process comprising:
(a) contacting fibrous protein with an alkaline solution;
(b) optionally removing excess alkaline solution from the fibrous protein;
(c) ageing the mixture of fibrous protein and alkaline solution to form a homogenous solution; and
(d) coagulating the solution obtained in (c) to form the proteinaceous material.

In one embodiment, the present invention provides a proteinaceous material prepared by a process comprising:
contacting fibrous protein with an alkaline solution;
removing excess alkaline solution from the fibrous protein;
ageing the mixture of fibrous protein and alkaline solution to form a homogenous solution; and
coagulating the homogenous solution to form the proteinaceous material.

In another embodiment, the present invention provides a proteinaceous material prepared by a process comprising:
contacting fibrous protein with an alkaline solution;
ageing the mixture of fibrous protein and alkaline solution to form a homogenous solution; and
coagulating the homogenous solution to form the proteinaceous material.

Although the present invention is broadly as defined above, those persons skilled in the art will appreciate that the invention is not limited thereto and that the invention also includes embodiments of which the following description gives examples.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

DETAILED DESCRIPTION

The term "comprising" as used in this specification means "consisting at least in part of". When interpreting statements in this specification which include that term, the features, prefaced by that term in each statement or claim, all need to be present but other features can also be present. Related terms such as "comprise" and "comprised" are to be interpreted in the same manner.

Unless otherwise specified, all solution concentrations herein are percent weight (g)/volume (ml) (% w/v).

The present invention broadly relates to a process for producing proteinaceous materials by solubilising fibrous protein then processing the resulting solution to produce, for example, reconstituted proteinaceous fibres, films, sheets, coatings, particles, shapes, foams or composites.

Accordingly, in some embodiments, the proteinaceous material comprises a fibre, film, sheet, coating, particle, shape, foam or composite. In some embodiments, the proteinaceous material comprises a flexible fibre, film or foam. In other embodiments, the proteinaceous material comprises a rigid shape, foam or composite.

Fibrous protein includes, but is not limited to, keratin, collagen, elastin and fibroin. In some embodiments, the fibrous protein comprises keratin or collagen or a mixture thereof. In some embodiments, the fibrous protein comprises keratin.

Suitable sources of keratin include, but are not limited to, wool, hair, horns, hooves and feathers. In some embodiments, the fibrous protein consists of wool, hair, or feathers, or a mixture of any two or more thereof. In some embodiments, the fibrous protein consists of wool or feathers, or a mixture thereof. In some embodiments, the fibrous protein comprises wool. In some embodiments, the fibrous protein consists essentially of wool. In some embodiments, the fibrous protein consists of wool.

Other suitable sources of fibrous protein include meat and skin. Suitable sources of collagen include, but are not limited to, sheep and cow skin.

In some embodiments, particularly wherein the fibrous protein is obtained from a material such as horns or hooves, the material may be comminuted prior to contact with the alkaline solution. Comminution increases the rate at which the alkaline solution solubilises the fibrous protein. In some embodiments, the material is comminuted such that the resulting fibrous protein starting material has at least one dimension that is about 50 microns or less.

The present description is substantially directed to methods that utilise wool. However, the invention can be applied to other fibrous protein.

Raw wool is typically scoured prior to being used in a process of the invention. The scouring process removes fat and grease. In some embodiments, the wool is scoured with detergents and sodium carbonate. Suitable detergents include, but are not limited to, alkylphenol ethoxylates (APEOs) and fatty alcohol ethoxylates. In some embodiments, the sodium carbonate is 10% aqueous sodium carbonate. The scouring process may also include bleaching the wool, for example with hydrogen peroxide.

The wool may also be combed and/or carded to remove leaves or other vegetable material. In some embodiments, this step is omitted. Such material may also be removed by filtering the mixture after ageing and before the coagulation step.

The first step of the process involves contacting fibrous protein with an alkaline solution. Preferably, the fibrous protein is wool.

In some embodiments, the pH of the alkaline solution is at least about 12. In some embodiments, the pH of the alkaline solution is at least about 13. In some embodiments, the pH of the alkaline solution is at least about 13.5. In some embodiments, the pH of the alkaline solution is about 14.

In some embodiments, the alkaline solution is an aqueous solution of an alkali metal hydroxide or alkaline earth metal hydroxide. In some embodiments, the hydroxide is selected from LiOH, NaOH, KOH and $Ca(OH)_2$.

In some embodiments, the alkaline solution is aqueous NaOH. In some embodiments, the concentration of NaOH is between about 2% and about 20%. In some embodiments, the concentration of NaOH is between about 2% and about 15%. In some embodiments, the concentration of NaOH is between about 2% and about 10%. In some embodiments, the concentration of NaOH is between about 5% and about 15%. In some embodiments, the concentration of NaOH is between about 5% and about 10%. In some embodiments, the concentration of NaOH is about 10%.

The concentration of NaOH may be varied depending on the fibrous protein. For example, compared to the concentration used when the fibrous protein comprises wool, when the fibrous protein comprises feathers the concentration is typically lower and when the fibrous protein comprises collagen the concentration is typically higher.

In some embodiments, wherein the fibrous protein is wool and the alkaline solution is aqueous NaOH, the properties of the proteinaceous material may vary with the concentration of the alkaline solution. In some embodiments, the tenacity (breaking strength) of fibres formed upon coagulation has been observed to be inversely proportional to the concentration of the alkaline solution.

In some embodiments, the alkaline solution is alcoholic alkali metal alkoxide. In some embodiments, the alkali metal alkoxide is sodium methoxide, sodium ethoxide, potassium methoxide or potassium ethoxide.

In some embodiments, the alkaline solution is ethanolic sodium ethoxide. Solutions of ethanolic sodium ethoxide are commercially available or may be prepared by, for example, dissolving commercially available sodium ethoxide pellets in ethanol or by reacting sodium metal with ethanol. In some embodiments, the concentration of sodium ethoxide is between about 5% and about 30%, or between about 10% and about 25%. In some embodiments, the concentration of sodium ethoxide is about 20%. Such a solution may be prepared by, for example, dissolving 20 g of sodium ethoxide pellets in 100 ml of ethanol.

In some embodiments, the alkaline solution is alcoholic alkali metal hydroxide. In some embodiments, the alkali metal hydroxide is NaOH or KOH.

In some embodiments, the alkaline solution is ethanolic NaOH. In some embodiments, the concentration of NaOH is between about 2% and about 30%, or between about 5% and about 30%, or between about 10% and about 25%, or about 10%. In some embodiments, the alkaline solution is 20% ethanolic NaOH. Such a solution may be prepared by, for example, dissolving 20 g of NaOH in 100 ml of ethanol.

Alcoholic alkali metal hydroxide solutions also comprise the alkali metal alkoxide. Such solutions typically comprise higher concentrations of water, which is formed from the reaction of the hydroxide with the alcohol, than do alkali metal alkoxide solutions prepared by, for example, dissolving the solid alkoxide in the alcohol or by reacting the alkali metal with the alcohol.

In some embodiments, the alkaline solution is an aqueous or alcoholic solution of a quaternary ammonium hydroxide. In some embodiments, the quaternary ammonium hydroxide is tetramethylammonium hydroxide or tetrabutylammonium hydroxide.

The fibrous protein is contacted with the alkaline solution for a time sufficient to saturate the protein with the alkaline solution. The fibrous protein may conveniently be contacted by immersing it into the alkaline solution. However, the invention is not limited thereto and other suitable methods will be apparent to those persons skilled in the art. In some embodiments, the fibrous protein is contacted with the alkaline solution by pouring or spraying the alkaline solution onto the fibrous protein.

The invention also contemplates embodiments in which the fibrous protein is immersed into a solvent, for example water, methanol or ethanol, to which an alkali, for example a solid alkali, is added to form the alkaline solution that contacts the fibrous protein.

In some embodiments, wherein the fibrous protein is immersed in the alkaline solution, the solution is foamed during immersion by, for example, rapid stirring.

In some embodiments, wherein wool is immersed into the alkaline solution and the alkaline solution is aqueous sodium hydroxide, the ratio of wool weight (in grams) to alkaline solution volume (in ml) is between about 1:3 and about 1:100, or between about 1:5 and about 1:50, or between about 1:5 and about 1:25. In some embodiments, wherein wool is immersed into the alkaline solution and the alkaline solution is aqueous sodium hydroxide, the ratio of wool weight (in grams) to alkaline solution volume (in ml) is about 1:20 or about 1:5.

In some embodiments, wherein skin, for example leather, or meat is immersed into the alkaline solution and the alkaline solution is aqueous sodium hydroxide, the ratio of skin or meat weight (in grams) to alkaline solution volume (in ml) is between about 1:3 and about 1:100, or between about 1:5 and about 1:50, or between about 1:5 and about 1:25, or about 1:20.

In some embodiments, wherein the alkaline solution is ethanolic sodium ethoxide or ethanolic sodium hydroxide, the ratio of wool weight (in grams) to alkaline solution volume (in ml) is between about 1:3 and about 1:100, or between about 1:5 and about 1:50, or between about 1:10 and about 1:50, or about 1:40.

In some embodiments, wherein the fibrous protein is immersed into the alkaline solution, the fibrous protein is immersed for a sufficient time to saturate the fibrous protein. In some embodiments, wherein alkaline solution is aqueous sodium hydroxide, the fibrous protein is immersed into the alkaline solution for up to about 120 seconds. In some embodiments, wherein alkaline solution is aqueous sodium hydroxide, the fibrous protein is immersed into the alkaline solution for up to about 60 seconds. In some embodiments, the immersion time is between about 45 seconds and about 60 seconds.

In some embodiments, wherein the fibrous protein is wool, the fibrous protein is contacted with the alkaline solution, preferably by being immersed into the alkaline solution, for up to about 5 minutes, or up to about 4 minutes, or up to about 3 minutes, or up to about 2 minutes, or up to about 1 minute, or between about 45 seconds and about 60 seconds, but the invention is not limited thereto and longer contact times may be used in other embodiments. In some of these embodiments, the alkaline solution is aqueous sodium hydroxide, preferably about 10% aqueous sodium hydroxide.

In other embodiments, wherein alkaline solution is ethanolic sodium ethoxide or ethanolic sodium hydroxide and the fibrous protein is wool, the fibrous protein is immersed into the alkaline solution for up to about 15 minutes, but the invention is not limited thereto and longer immersion times may be used in other embodiments. In some embodiments, the immersion time is between about 10 minutes and about 15 minutes.

In some embodiments, the fibrous protein is agitated, stirred or otherwise mixed with the alkaline solution such that it is completely saturated with the alkaline solution.

In some embodiments, the fibrous protein is placed in a porous container, such as a wire-mesh container or sieve, and immersed in the alkaline solution while the container is rotated, or the sieve is stirred, in the alkaline solution.

In some embodiments, for example those in which the fibrous protein is contacted with the alkaline solution by immersion, after contacting the fibrous protein with the alkaline solution, the excess alkaline solution is removed from the fibrous protein.

Wool, for example, typically absorbs about 35-40% by weight of water. Following removal of the excess alkaline solution, the wool is preferably moist with the alkaline solution without further liquid leaking or dripping from the wool.

In some embodiments, the excess alkaline solution is removed by pressing the fibrous protein. The fibrous protein may be pressed using, for example, a press suitable for removing excess NaOH solution from alkali-cellulose in the viscose process.

In other embodiments, the excess alkaline solution is removed by, for example, wringing the fibrous protein or by subjecting the fibrous protein to centrifugal force.

In some embodiments, after removal of excess alkaline solution, the mixture of wool and alkaline solution comprises at least about 30% to about 40% alkaline solution by the initial weight of the wool. In some embodiments, wherein the alkaline solution is 10% aqueous NaOH, the mixture of wool and alkaline solution comprises about 100% to about 130% alkaline solution by the initial weight of the wool.

In some embodiments, the mixture of wool and alkaline solution comprises between about 50% and about 200%, or between about 70% and about 180%, or between about 80% and about 180%, or between about 90% and about 160%, or between about 100% and about 150%, or between about 100% and about 130%, or about 150% alkaline solution by the initial weight of the wool. In some of these embodiments, the alkaline solution is aqueous sodium hydroxide, preferably about 10% aqueous sodium hydroxide.

In some embodiments, wherein the alkaline solution is 20% ethanolic sodium ethoxide or 20% ethanolic sodium hydroxide, after removal of excess alkaline solution, the mixture of wool and alkaline solution comprises about 88% to about 100% alkaline solution by the initial weight of the wool. In some embodiments, the mixture of wool and alkaline solution comprises between about 50% and about 150%, or between about 60% and about 140%, or between about 70% and about 120% alkaline solution by the initial weight of the wool.

In some embodiments, step (b) is omitted.

In some embodiments, wherein wool is immersed into aqueous sodium hydroxide and step (b) is omitted, the ratio of wool weight (in grams) to alkaline solution volume (in ml) is about 1:5.

In some embodiments, wherein the fibrous protein is wool and step (b) is omitted, the ratio of wool weight (in grams) to alkaline solution volume (in ml) is between about 1:2 and about 1:10, in other embodiments between about 1:3 and about 1:8, and in other embodiments between about 1:4 and about 1:6. In some of these embodiments, the alkaline solution is aqueous sodium hydroxide, preferably about 10% aqueous sodium hydroxide.

After the excess alkaline solution has been removed from the fibrous protein, the mixture of fibrous protein and alkaline solution is aged. In those embodiments wherein step (b) is omitted, the ageing step follows the contacting step. During the ageing step, the alkaline solution reacts with the fibrous protein dissolving it to typically first form a paste and then a viscous homogenous solution.

Advantageously, the contacting and ageing steps may be performed at ambient (room) temperature, typically about 20° C. to about 25° C. Temperatures outside this range may, however, be useful in some embodiments. Those persons skilled in the art will appreciate that the rate of hydrolysis of the fibrous protein will increase with increasing temperature.

The mixture of fibrous protein and alkaline solution may be aged for about 15 to about 180 minutes, although times outside these ranges may be useful in some embodiments. In some embodiments, the mixture is aged for at least about 15 minutes.

The ageing time generally depends on the nature of the fibrous protein, the concentration of the alkaline solution, and the particular alkali. The ageing time is generally longer for those embodiments in which the alkaline solution is ethanolic sodium ethoxide or ethanolic sodium hydroxide compared to aqueous NaOH. In addition, the ageing time may depend on whether step (b) is omitted. The ageing time is generally longer in those embodiments in which step (b) is performed compared to those embodiments in which step (b) is omitted.

In some embodiments, wherein the fibrous protein is skin, for example leather, the mixture of fibrous protein and alkaline solution is aged for about 4 hours or more. In some embodiments, wherein the fibrous protein is meat, the mixture of fibrous protein and alkaline solution is aged for about 6 hours or more. In some embodiments wherein the fibrous protein is leather or meat, the mixture of fibrous protein and alkaline solution is aged for at least about 8 hours. In some of these embodiments, the alkaline solution is aqueous NaOH, preferably about 10% aqueous NaOH.

In some embodiments, wherein the fibrous protein is wool and the alkaline solution is aqueous NaOH, the mixture of fibrous protein and alkaline solution is aged for between about 15 minutes and about 180 minutes, in some embodiments between about 15 minutes and about 150 minutes. In some embodiments, wherein the alkaline solution is 5% aqueous NaOH, the mixture is aged for between about 15 minutes and about 120 minutes.

In some embodiments, wherein the fibrous protein is wool and the alkaline solution is 10% aqueous NaOH, the mixture is aged for between about 15 minutes and about 120 minutes. In some embodiments, the mixture is aged for between about 15 minutes and about 90 minutes, or between about 45 minutes and about 60 minutes.

In some embodiments, wherein the fibrous protein is wool and the alkaline solution is 20% ethanolic sodium ethoxide or 20% ethanolic sodium hydroxide, the mixture of fibrous protein and alkaline solution is aged for about 180 minutes.

The fibrous protein may be mechanically stirred or agitated during the ageing step, particularly in those embodiments wherein the fibrous protein comprises skin or meat.

In some embodiments, wherein step (b) is performed and the fibrous protein is wool, the mixture of wool and alkaline solution is aged for between about 15 minutes and about 180 minutes, or between about 30 minutes and about 150 minutes, or between about 30 minutes and about 120 minutes, or between about 40 minutes and about 100 minutes, or between about 45 minutes and about 90 minutes. In some of these embodiments, the alkaline solution is aqueous NaOH, preferably about 10% aqueous NaOH.

In some embodiments, wherein step (b) is omitted and the fibrous protein is wool, the wool and alkaline solution are contacted, preferably by immersing the wool in the alkaline solution, and aged for between about 15 minutes and about 180 minutes, or between about 30 minutes and about 150 minutes, or between about 30 minutes and about 120 minutes, or between about 40 minutes and about 100 minutes, or between about 40 minutes and about 90 minutes, or between about 40 minutes and about 70 minutes, or between about 45 minutes and about 70 minutes, or between about 45 minutes and about 65 minutes. In some of these embodiments, the alkaline solution is aqueous NaOH, preferably about 10% aqueous NaOH.

Optionally, the aged mixture is filtered to remove physical impurities and provide a homogenous solution. For example, when the fibrous protein comprises wool, the mixture may be filtered to remove leaves or other vegetable material. Filtering may also be used to remove the undissolved quills when the fibrous protein comprises feathers.

The homogenous solution obtained following the ageing step typically has the consistency of viscous honey. In some embodiments, the homogenous solution has a viscosity between about 5,000 cP and about 20,000 cP, but the invention is not limited thereto and homogenous solutions having viscosities outside this range may be useful in some embodiments. In some embodiments, the homogenous solution has a viscosity between about 5,000 cP and about 15,000 cP. In some embodiments, the homogenous solution has a viscosity between about 10,000 cP and about 15,000 cP.

Without wishing to be bound by theory, it is thought that the reaction of the fibrous protein with the alkaline solution proceeds in two stages, dissolution then hydrolysis, the rate of which depends on the concentration and amount of alkaline solution. In the process of the invention, the homogenous solution that is formed in step (c) is coagulated in step (d) before complete hydrolysis of the fibrous protein starting material. Accordingly, in the present invention, the peptide chains and, preferably, the disulfide linkages in the fibrous protein starting material are not completely hydrolysed prior to the coagulating step.

Extended contact between the fibrous protein and the bulk alkaline solution will lead to complete hydrolysis of the fibrous protein. For example, steeping 2 grams of wool in 20-40 ml of 20% aqueous NaOH results in the complete hydrolysis of the wool to its constituent amino acids. Such an amino acid solution is generally not suitable for coagulation to form the proteinaceous material of the invention.

In some embodiments, the use of alcoholic alkali metal alkoxide or alcoholic metal hydroxide may be advantageous. The alcohol solvent may assist in solubilising the fibrous protein as it reacts with the alkaline solution and the reduced water content, compared with aqueous alkaline solutions, may slow the rate at which the protein hydrolyses. For example, 1 gram of wool must be steeped for longer than six hours in 20 ml of 20% ethanolic sodium ethoxide for complete hydrolysis. Reducing the rate of hydrolysis generally enables the production of proteinaceous material with a higher degree of polymerisation. In addition, a reduced rate of hydrolysis is desirable in some embodiments because the resulting mixture of fibrous protein and alkaline solution is more stable such that the time between the contacting step and the coagulation step can be extended.

The homogenous solution may be stored by freezing, and then thawed prior to further processing.

In those embodiments wherein the excess alkaline solution is removed, for example by pressing the fibrous protein, the homogenous solution may be stored in a humid environment prior to further processing. In some embodiments, the homogenous solution may be stored in a humid environment for about 2 days. In some embodiments, the homogenous solution may be stored in a humid environment for about 1 day.

The homogenous solution is then coagulated to form the proteinaceous material. During the coagulation step, the homogenous solution is typically treated with acid to neutralise the alkali and form the solid proteinaceous material. Alternatively, the homogenous solution may be treated with another reagent, for example an acyl halide or acid anhydride, to form the solid proteinaceous material.

In some embodiments, two or more homogenous solutions prepared from the same or different fibrous protein starting materials may be combined before being coagulated. In some embodiments, a homogenous solution formed from wool is combined with a homogenous solution formed from collagen. In other embodiments, a homogenous solution formed from wool is combined with a homogenous solution formed from feathers. In some embodiments, equivalent quantities of the homogenous solutions are combined.

A homogenous solution may also be prepared from a protein other than a fibrous protein using a process analogous to that described above. The invention contemplates embodiments wherein one or more of such a homogenous solution is combined with one or more homogenous solution prepared from a fibrous protein according to the process described above and then coagulated to form a proteinaceous material. For example, a homogenous solution formed from soy protein may be combined with a homogenous solution formed from wool. In other embodiments, the only protein from which the homogenous solution that is coagulated to form the proteinaceous material is prepared is one or more fibrous protein.

In some embodiments, the homogenous solution is coagulated by immersion in a coagulation bath in which the proteinaceous material is insoluble.

In some embodiments, the homogenous solution is coagulated by treating the solution with a liquid coagulant. In some embodiments, the liquid coagulant comprises an acid or a solution thereof. In some embodiments, the liquid coagulant comprises an acyl halide or acid anhydride, or a solution thereof.

In some embodiments, the homogenous solution is coagulated by treating the solution with a solid coagulant which, in some embodiments, comprises an acid.

In some embodiments, the solid coagulant is selected from the group consisting of oxalic acid, benzoic acid, terephthalic acid, phthalic acid, isophthalic acid, and salicylic acid. In some embodiments, the solid coagulant is oxalic acid. In some embodiments, wherein the fibrous protein is wool, the fibrous protein:oxalic acid ratio (w/w) is between about 3:1 and about 1:3, or between about 2:1 and about 1:2. In some embodiments, wherein the fibrous protein is wool, the fibrous protein:oxalic acid ratio (w/w) is about 1:1. The resulting proteinaceous material is thought to comprise thiooxalate functional groups.

After treating the homogenous solution with the solid coagulant or during treatment of the homogenous solution with the solid coagulant, typically by mixing the solid into the homogenous solution, the resulting mixture may be cast into a mould or frame. In this way, the proteinaceous material may be obtained as a solid form in any desirable shape. Any water resulting from the formation of the proteinaceous material may be poured out of the mould or frame.

In some embodiments, the homogenous solution is cast into a mould or frame prior to immersion in a coagulation bath. In this way, the proteinaceous material may be obtained as a solid form in any desirable shape.

The solid proteinaceous material may also be shaped after coagulation. In some embodiments, the solid proteinaceous material is shaped by pressing into a mould.

The mould containing the homogenous solution is typically immersed in the coagulation bath for a time sufficient to form the solid proteinaceous material. The immersion time may depend on both the composition of the coagulation bath, for example the pH, and the size and shape of the cast homogenous solution. For example, the thicker the cast homogenous solution, the longer the immersion time required to form the proteinaceous material. In some embodiments, the mould containing the homogenous solution is immersed in the coagulation bath for between about 5 and about 6 hours.

In some embodiments, the homogenous solution is cast onto a substrate prior to immersion in a coagulation bath. In some embodiments, the substrate is glass, but the invention is not limited thereto and other substrates may also be used. In this way the proteinaceous material may be obtained as a film, a sheet or a coating. In some embodiments, the proteinaceous material is removed from the substrate after coagulation to provide the proteinaceous material as a film or a sheet.

The substrate on which the homogenous solution has been cast is typically immersed in the coagulation bath for a time sufficient to form the solid proteinaceous material. The immersion time will depend on both the composition of the coagulation bath, for example the pH, and the thickness of the cast homogenous solution. For example, the thicker the cast homogenous solution, the longer the immersion time required to form the proteinaceous material. In some embodiments, the mould containing the substrate on which the homogenous solution has been cast is immersed in the coagulation bath for between about 5 minutes and about 30 minutes, or between about 10 minutes and about 25 minutes, or about 20 minutes.

In some embodiments, the homogenous solution is cast onto an acidic substrate and coagulates to form the solid proteinaceous material. The homogenous solution may also be sprayed onto an acidic substrate.

In some embodiments, the homogenous solution is coagulated by extrusion into a coagulation bath in which the proteinaceous material is insoluble.

In some embodiments, the viscosity of the homogenous solution is adjusted before coagulation, which in some embodiments is by extrusion into the coagulation bath. The viscosity may be adjusted before or after the optional filtering step. In some embodiments, the viscosity of the homogenous solution is reduced by dilution with 2% aqueous NaOH. In other embodiments, the viscosity of the homogenous solution is reduced by dilution with water, preferably distilled water. The invention is not, however, limited thereto and other liquids may be used to reduce the viscosity of the homogenous solution.

In some embodiments, for example wherein wool is immersed into 10% aqueous sodium hydroxide and step (b) is omitted, and the ratio of wool weight (in grams) to alkaline solution volume (in ml) is about 1:5, the viscosity of the homogenous solution is decreased by adding an equal volume of water.

The coagulation bath comprises sufficient acid to neutralise the alkali and form the solid proteinaceous material. Alternatively, the coagulation bath comprises another reagent that reacts with the homogenous solution to form the solid proteinaceous material. In some embodiments, the coagulation bath comprises an acyl halide or acid anhydride.

In some embodiments, the acid is selected from the group consisting of sulfuric acid, hydrochloric acid, nitric acid, formic acid, phosphoric acid, acetic acid, oxalic acid, benzoic acid, terephthalic acid, phthalic acid, isophthalic acid, salicylic acid, ammonium sulfate and hydrogen peroxide. In some embodiments, the acid is selected from the group consisting of sulfuric acid, hydrochloric acid, nitric acid, formic acid, phosphoric acid, acetic acid, ammonium sulfate and hydrogen peroxide. In some embodiments, the acid is selected from the group consisting of sulfuric acid, hydrochloric acid, nitric acid, formic acid, phosphoric acid and acetic acid. In some embodiments, the acid is sulfuric acid. In other embodiments, the acid is acetic acid. In other embodiments, the acid is oxalic acid.

In some embodiments, the coagulation bath further comprises sodium sulfate. In some embodiments, the coagulation bath comprises between about 10% and about 40%, or between about 15% and about 40%, or between about 20% and about 40% sodium sulfate. In some embodiments, the coagulation bath comprises at least about 20% sodium sulfate. In some embodiments, the coagulation bath comprises about 35% sodium sulfate.

In some embodiments, the coagulation bath further comprises zinc sulfate. Zinc sulfate may promote coagulation and, in those embodiments wherein the proteinaceous material is obtained as a fibre, crenulation of the resulting fibre. In some embodiments, the coagulation bath comprises between about 0.01% and about 1%, or between about 0.05% and about 0.5% zinc sulfate. In some embodiments, the coagulation bath comprises about 0.1% zinc sulfate.

In some embodiments, the coagulation bath comprises sulfuric acid. In some embodiments, the coagulation bath comprises at least about 5% sulfuric acid. In some embodiments, the coagulation bath comprises at least about 10% sulfuric acid. In some embodiments, the coagulation bath comprises at least about 11% sulfuric acid. In some embodiments, the coagulation bath comprises an aqueous solution of sulfuric acid and sodium sulfate. In some embodiments, the coagulation bath comprises an aqueous solution of sulfuric acid, sodium sulfate and zinc sulfate. In some embodiments, the coagulation bath comprises about 110 g/l sulfuric acid, about 350 g/l sodium sulfate and about 10 g/l zinc sulfate.

In some embodiments, the coagulation bath comprises an aqueous solution of ammonium sulfate. In some embodiments, the coagulation bath comprises between about 10% and about 40%, or between about 15% and about 40%, or between about 20% and about 35% aqueous ammonium sulfate. In some embodiments, the coagulation bath comprises about 30% aqueous ammonium sulfate.

In some embodiments, the coagulation bath comprises an aqueous solution of ammonium sulfate and sodium sulfate. In some embodiments, the coagulation bath comprises about 20% ammonium sulfate and about 20% sodium sulfate.

In some embodiments, the coagulation bath comprises acetic acid. In some embodiments, the coagulation bath comprises glacial acetic acid. In some embodiments, the coagulation bath comprises between about 50% and about 100%, or between about 55% and about 95% acetic acid. In some embodiments, the coagulation bath comprises about 60% to about 80% acetic acid.

In some embodiments, the coagulation bath comprises an acid selected from the group consisting of oxalic acid, benzoic acid, terephthalic acid, phthalic acid, isophthalic acid, and salicylic acid. These weak acids are typically used in the coagulation bath together with a strong acid, such as sulfuric acid. In some embodiments, wherein the weak acid is water soluble, the coagulation bath comprises between about 2% and about 14%, or between about 3% and about 10%, or between about 4% and about 6%, or about 5% of the weak acid. In some embodiments, wherein the weak acid, for example terephthalic acid, is poorly water soluble, but soluble in ethanol, the coagulation bath comprises between about 1% and about 10%, or between about 1% and about 5%, or about 2% of the weak acid, and the weak acid is added to the coagulation bath as, for example, a 20% ethanolic solution. In some embodiments, the coagulation bath comprises about 20 g/l terephthalic acid, about 110 g/l sulfuric acid, about 350 g/l sodium sulfate, about 10 g/l zinc sulfate, and about 100 ml/l ethanol.

In some embodiments, the coagulation bath comprises oxalic acid. In some embodiments, the coagulation bath comprises between about 2% and about 14%, or between about 3% and about 10%, or between about 4% and about 6% oxalic acid. In some embodiments, the coagulation bath comprises about 5% oxalic acid. In some embodiments, the coagulation bath comprises about 50 g/l oxalic acid, about 110 g/l sulfuric acid, about 350 g/l sodium sulfate and about 10 g/l zinc sulfate.

In some embodiments, the coagulation bath comprises hydrogen peroxide. In some embodiments, the coagulation bath comprises about 30% hydrogen peroxide.

In those embodiments wherein the fibrous protein is naturally coloured wool, such as black or brown wool, the use of a coagulation bath comprising hydrogen peroxide may hinder the formation of disulfide linkages such that the resulting proteinaceous material is colourless.

In some embodiments, the coagulation bath comprises an acyl halide, which in some embodiments is an acyl chloride, or an acid anhydride.

Without wishing to be bound by theory, it is thought that the reaction of the fibrous protein with the alkaline solution to form the homogenous solution results in at least some of the free thiol groups in the fibrous protein being converted to thiolates. This conversion is thought to be reversed in the acid conditions used during coagulation of the homogenous solution in some embodiments. The free thiol groups present in the homogenous solution may, however, also react with, for example, various carboxylic acids, acyl halides and acid anhydrides to form, for example, proteinaceous materials comprising thioesters.

Various acyl halides and acid anhydrides are liquids at ambient conditions. Accordingly, in some embodiments, the coagulation bath consists essentially of an acyl halide, which in some embodiments is an acyl chloride, or an acid anhydride.

In some embodiments, the coagulation bath consists essentially of benzoyl chloride. The resulting proteinaceous material is thought to comprise thiobenzoate functional groups.

In some embodiments, the coagulation bath consists essentially of acetyl chloride. In some embodiments, the coagulation bath consists essentially of acetic anhydride. In these embodiments, the resulting proteinaceous materials are thought to comprise thioacetate functional groups.

Various acyl halides and acid anhydrides are solids at ambient conditions. Accordingly, in some embodiments, the coagulation bath comprises a solution of an acyl halide, which in some embodiments is an acyl chloride, or an acid anhydride, in a solvent. Suitable solvents include ethanol, preferably having a purity of at least about 98%.

In some embodiments, the coagulation bath comprises ethanolic terephthaloyl dichloride. In some embodiments, the coagulation bath comprises between about 5% and about 20%, or between about 10% and about 20%, or about 10% ethanolic terephthaloyl dichloride. The resulting proteinaceous material is thought to comprise thioterephthalate functional groups. Such a coagulation bath may be prepared by, for example, dissolving the terephthaloyl dichloride in ethanol with heating and then cooling the resulting mixture prior to use.

In some embodiments wherein the coagulation bath comprises an acyl halide or an acid anhydride, the homogenous solution:coagulation bath ratio (v/v) is about 1:10 or 1:20. In other embodiments, the ratio is between about 1:5 and about 1:100, or between about 1:5 and about 1:50, or between about 1:7 and about 1:30.

Those persons skilled in the art will appreciate that the homogenous solution can be extruded into a coagulation bath in any shape such that the proteinaceous material can be formed, for example, as a fibre, film, sheet, coating or as a particle.

In some embodiments, the homogenous solution is formed into a film by extrusion through a narrow slit into a coagulation bath.

In some embodiments, the homogenous solution is formed into fibres using a conventional wet spinning machine typically used for viscose. In these embodiments, the solution is forced through a spinneret into a coagulation bath.

Advantageously, the wet spinning process enables the production of fibres of any desired diameter by selecting the appropriate spinneret. The resulting fibres have a consistent diameter and may be produced as single long filaments. This is in contrast to naturally occurring fibres, such as wool, which form as staples and for which the diameter is variable and the length limited.

In some embodiments, the fibres are extruded with a diameter of approximately ten microns or less. Such fibres provide the same level of comfort and freedom from prickle as fine cashmere, cotton or polar fleece, and are suitable for high end apparel usage.

As noted above, the viscosity of the homogenous solution may be adjusted. When the homogenous solution is to be wet spun, those persons skilled in the art can adjust the viscosity to give the desired flow rate through the spinneret in view of the velocity of the pickup rollers.

Fibres obtained using a coagulation bath comprising acetic acid may be softer than those obtained using a sulfuric acid coagulation bath. Fibres obtained using an ammonium sulfate coagulation bath may be stronger than those obtained using a sulfuric acid coagulation bath.

In some embodiments, wherein the homogenous solution is wet spun, the coagulation bath comprises ammonium sulfate or other weak acid. The rate of coagulation is reduced in a coagulation bath comprising a weak acid compared to a strong acid, such as sulfuric acid. Reducing the rate of coagulation permits the fibre to be subjected to greater stretch during the wet spinning.

After extrusion into the coagulation bath, the proteinaceous material is collected from the bath.

After removal from the coagulation bath, the proteinaceous material may be washed with an alkaline solution, such as aqueous sodium carbonate, to neutralize the acid. Suitable alkaline solutions include, but are not limited to, 10% aqueous sodium carbonate and 20% aqueous sodium carbonate. In other embodiments, the proteinaceous material is washed with water. The proteinaceous material may then be air dried.

In those embodiments wherein the proteinaceous material is formed as fibres, the fibres may be wound onto a bobbin. The fibres may also be cut if short staple fibres are required.

In some embodiments, the proteinaceous material may be formed as a plurality of short fibres by, for example, rapidly forcing the homogenous solution through a spinneret into the coagulation bath.

Optionally, the proteinaceous material, which in some embodiments is formed as fibres, may be subjected to additional treatments depending on its intended application. For example, treating the fibres with aqueous formaldehyde, such as a 30% aqueous formaldehyde solution, will stiffen them. Similarly, immersing a solid form, foam or film comprising the proteinaceous material in aqueous formaldehyde will harden the solid form, foam or film. The immersion time will depend on both the concentration of the formaldehyde solution and the size and shape of the proteinaceous material. In some embodiments, the proteinaceous material is immersed in a 30% aqueous formaldehyde solution for about one day, then rinsed with water prior to drying.

Other aldehydes, for example aqueous acetaldehyde, may also be used to harden the proteinaceous material. In some embodiments, the aqueous acetaldehyde is 35% aqueous acetaldehyde.

The resulting fibres resemble wool or silk. When the fibrous protein starting material is wool, the resulting fibres retain the chemical properties of wool, but lack the fibre structure of wool.

The proteinaceous material may be subjected to other treatments. In some embodiments, the proteinaceous material is dyed with dyes conventionally used for dyeing protein fibres such as acid dyes.

In some embodiments, the degree of polymerization of the resulting fibres is less than that of the fibrous protein starting material. When the starting material is wool, the resulting fibres may have a degree of polymerisation comparable to that of viscose or cotton.

The proteinaceous material may be further processed.

In some embodiments, the proteinaceous material is ground to a powder using, for example, a conventional electrically-powered grinder.

The homogenous solution may be combined with various additives prior to coagulation to form the proteinaceous material.

For example, the homogenous solution may be coloured with suitable dyes or pigments that are stable under both the alkaline conditions of the homogenous solution and the conditions of the coagulation bath.

In some embodiments, one or more plasticiser is added to the homogenous solution prior to coagulation. Suitable plasticisers include, for example, carboxymethyl cellulose (CMC), polyvinyl acetate (PVA) and polyethylene glycol (PEG). Preferred PEGs are water soluble. In one embodiment, the plasticiser is PEG 6000, which may be added to the homogenous solution as a 20% aqueous solution. In some embodiments, wherein the fibrous protein is wool, the fibrous protein:PEG 6000 ratio (w/w) is between about 5:1 and about 1:1, or about 2.5:1. In some embodiments, wherein the fibrous protein is wool, the fibrous protein:CMC or PVA ratio (w/w) is between about 5:1 and about 1:1, or between about 4:1 and about 2:1.

In some embodiments, urea ($CO(NH_2)_2$) or a functional analogue thereof is added to the homogenous solution prior to coagulation. In some embodiments, wherein the fibrous protein is wool, the fibrous protein:urea ratio is between about 2:1 and about 1:2, or about 1:1.

Urea is highly water soluble, which reflects its ability to engage in extensive hydrogen bonding with water. Without wishing to be bound by theory, it is thought that the reaction of the fibrous protein with the alkaline solution disrupts the hydrogen bonding network in the protein. Upon coagulation, the resulting proteinaceous material tends to be less flexible than the fibrous protein. The plasticiser, if used, occupies space between the chains of protein polymers formed upon coagulation, increasing the free volume (vf) and lowering the glass transition temperature for the proteinaceous material, making it softer and more flexible. In contrast, addition of urea is thought to result in an extensive network of hydrogen bonds in the proteinaceous material formed upon coagulation of the homogenous solution, increasing the vf. This hydrogen bonding network results in the proteinaceous material having greater flexibility than equivalent material formed without addition of urea.

The invention also contemplates embodiments in which one or more plasticiser and urea are added to the homogenous solution.

The homogenous solution may be chemically modified prior to coagulation to form the proteinaceous material.

For example, it is thought that the free thiol groups present in the homogenous solution may react with various reagents such as carboxylic acids and their salts to form, for example, thioesters. In those embodiments wherein a carboxylic acid salt is added to the homogenous solution it is thought that, upon reaction with acid in the coagulation bath, the carboxylic acid salts are converted to the acid, which then reacts with the free thiol groups.

In some embodiments, an organic acid is added to the homogenous solution prior to coagulation. In some embodiments, a salt of an organic acid or a salt of an inorganic acid is added to the homogenous solution prior to coagulation. In some embodiments, the salt is a sodium or potassium salt.

In those embodiments wherein an organic acid is added to the homogenous solution prior to coagulation, the amount of organic acid is selected to be less than that required to neutralize the alkali and coagulate the proteinaceous material. The chemically modified homogenous solution may then be coagulated to form the proteinaceous material In some embodiments, a silicate salt, such as a sodium silicate, is added to the homogenous solution prior to coagulation. Such silicate salts may improve the thermal properties of the proteinaceous material. In some embodiments, a phosphate salt, such as sodium pyrophosphate, is added to the homogenous solution prior to coagulation. Such phosphate salts may maintain the colour, and improve the thermal properties, of the proteinaceous material.

In some embodiments, a carboxylic acid or a salt thereof is added to the homogenous solution prior to coagulation. In some embodiments, the carboxylic acid is an aliphatic carboxylic acid. In some embodiments, the carboxylic acid is an aromatic carboxylic acid. In some embodiments, the salt is a sodium or potassium salt.

In some embodiments, sodium acetate is added to homogenous solution. In some embodiments, wherein the fibrous protein is wool, the fibrous protein:sodium acetate ratio (w/w) is between about 4:1 and about 1:1, or about 2:1. After coagulation, the proteinaceous material is thought to comprise thioacetate functional groups.

In some embodiments, monosodium phthalate is added to homogenous solution. In some embodiments, wherein the fibrous protein is wool, the fibrous protein:monosodium phthalate ratio (w/w) is between about 4:1 and about 1:1, or about 2:1. After coagulation, the proteinaceous material is thought to comprise thiophthalate functional groups.

In some embodiments, trisodium benzene-1,3,5-tricarboxylate is added to homogenous solution. In some embodiments, wherein the fibrous protein is wool, the fibrous protein:trisodium benzene-1,3,5-tricarboxylate ratio (w/w) is between about 4:1 and about 1:1, or about 2:1.

In other embodiments, disodium benzene-1,3,5-tricarboxylate or monosodium benzene-1,3,5-tricarboxylate is added to homogenous solution. In some embodiments, wherein the fibrous protein is wool, the fibrous protein:disodium benzene-1,3,5-tricarboxylate or monosodium benzene-1,3,5-tricarboxylate ratio (w/w) is between about 4:1 and about 1:1, or about 2:1.

In other embodiments, benzene-1,3,5-tricarboxylic acid is added to homogenous solution. In some embodiments, wherein the fibrous protein is wool, the fibrous protein:benzene-1,3,5-tricarboxylic acid ratio (w/w) is between about 5:1 and about 1:1, or between about 4:1 and about 2:1.

In some embodiments, benzoic acid or sodium benzoate is added to homogenous solution. In some embodiments, wherein the fibrous protein is wool, the fibrous protein:benzoic acid or sodium benzoate ratio (w/w) is between about 4:1 and about 1:1, or about 2:1.

In some embodiments, terephthalic acid is added to homogenous solution. In some embodiments, wherein the fibrous protein is wool, the fibrous protein:terephthalic acid ratio (w/w) is between about 4:1 and about 1:1, or about 2:1.

In some embodiments, isophthalic acid is added to homogenous solution. In some embodiments, wherein the fibrous protein is wool, the fibrous protein:isophthalic acid ratio (w/w) is between about 4:1 and about 1:1, or about 2:1.

In some embodiments, sodium terephthalate is added to homogenous solution. Sodium terephthalate is commercially available or may be recovered by saponification of PET (polyethylene terephthalate). In some embodiments, wherein the fibrous protein is wool, the fibrous protein:sodium terephthalate ratio (w/w) is between about 4:1 and about 1:1, or about 2:1.

In some embodiments, a sodium silicate is added to homogenous solution.

In some embodiments, sodium metasilicate ($Na_2SiO_3$) is added to homogenous solution. The sodium metasilicate may conveniently be added as an aqueous solution. In some embodiments, wherein the fibrous protein is wool, the fibrous protein:sodium metasilicate ratio (w/w) is between about 4:1 and about 1:1, or about 2:1.

In some embodiments, sodium orthosilicate ($Na_4SiO_4$) is added to homogenous solution. In some embodiments, wherein the fibrous protein is wool, the fibrous protein:sodium orthosilicate ratio (w/w) is between about 4:1 and about 1:1, or about 2:1.

In some embodiments, sodium pyrosilicate ($Na_6Si_2O_7$) is added to homogenous solution. In some embodiments, wherein the fibrous protein is wool, the fibrous protein:sodium pyrosilicate ratio (w/w) is between about 4:1 and about 1:1, or about 2:1.

The invention also contemplates embodiments in which the homogenous solution is combined with one or more other polymer prior to coagulation, such that the proteinaceous material comprises a polymer blend. The invention also contemplates embodiments in which the homogenous solution is combined with one or more other polymer precursor prior to coagulation, such that the proteinaceous material comprises a polymer blend. The invention also contemplates embodiments in which the homogenous solution is combined with one or more other polymer and one or more other polymer precursor prior to coagulation, such that the proteinaceous material comprises a polymer blend. In some embodiments, the homogenous solution may be chemically modified, as described above, prior to or after being combined with one or more other polymer and/or polymer precursor, and prior to coagulation.

In some embodiments, the homogenous solution is combined with polystyrene prior to coagulation. In some embodiments, the polystyrene is added as a 20% solution of polystyrene in ethyl acetate. In some embodiments, the homogenous solution is mixed with aqueous ethanol, preferably 70% aqueous ethanol, before adding the polystyrene solution. In some embodiments, wherein the fibrous protein is wool, and the homogenous solution comprises 20% wool, the homogenous solution:70% aqueous ethanol:polystyrene solution ratio (v/v/v) is about 5:1:5.

In some embodiments, the homogenous solution is combined with sodium cellulose xanthate prior to coagulation. Cellulose xanthate is a water-soluble thio-carbonate ester of cellulose which is dissolved in sodium hydroxide to form viscose. Viscose is conventionally coagulated in sulfuric acid to form regenerated cellulose, for example as rayon or cellophane.

In some embodiments, the sodium cellulose xanthate is added as a 20% solution of sodium cellulose xanthate in 20% aqueous NaOH. In some embodiments, wherein the fibrous protein is wool, and the homogenous solution comprises 20% wool, the homogenous solution:sodium cellulose xanthate solution ratio (v/v) is between about 9:1 and about 1:9, or about 1:1.

The proteinaceous material may be reinforced by, for example, adding glass fibres or carbon fibres to the homogenous solution prior to coagulation. In some embodiments, the homogenous solution is chemically modified and/or combined with one or more other polymer precursor and/or polymer and/or one or more other additive, as described above. After coagulation of the homogenous solution/fibre mixture, a glass fibre reinforced proteinaceous material or carbon fibre reinforced composite proteinaceous material is formed. In some embodiments, glass fibres are added to homogenous solution. In some embodiments, wherein the fibrous protein is wool, the fibrous protein:glass fibre ratio (w/w) is between about 4:1 and about 1:2, or between about 2:1 and about 1:1.

The glass fibres or carbon fibres may be added in the form of loose fibres. Alternatively, in some embodiments, the homogenous solution may be used as a resin with glass fibre or carbon fibre cloths to form articles that are then cured by coagulating the homogenous solution.

In some embodiments, the proteinaceous material is formed as a foam. In these embodiments, a blowing agent is added to the homogenous solution prior to coagulation. In some embodiments, the homogenous solution is chemically modified and/or combined with one or more other polymer precursor and/or polymer and/or one or more other additive, as described above.

Accordingly, the invention also contemplates embodiments in which the homogenous solution is combined with another polymer precursor and a blowing agent added prior to coagulation. The invention also contemplates embodiments in which the homogenous solution is combined with a polymer and a blowing agent added prior to coagulation. The invention also contemplates embodiments in which the homogenous solution is combined with another additive and a blowing agent added prior to coagulation.

In embodiments, the proteinaceous material is produced as a flexible foam and, in other embodiments, as a rigid foam.

The flexibility of the foam may be increased using one or more plasticisers and/or urea, as described above. The foam may also be treated with an aldehyde to harden it, as described above.

In some embodiments, the blowing agent is a physical blowing agent. Physical blowing agents include hydrochlorofluorocarbons (HCFCs), various hydrocarbons, such as butane, and $CO_2$.

In some embodiments, the blowing agent is a chemical blowing agent that reacts to form a gas during subsequent processing. In some embodiments, the chemical blowing agent reacts with the acid in the coagulation bath to form a gas which, in some embodiments, is $CO_2$.

In some embodiments, the chemical blowing agent is selected from the group consisting of carbonate salts, such as sodium carbonate, potassium carbonate and calcium carbonate, and carbonate esters, such as diethyl carbonate, sodium ethyl carbonate, potassium ethyl carbonate and ethylene carbonate, and combinations of any two or more thereof. Advantageously, the carbonate esters are thought to assist in cross-linking the proteinaceous material in addition to forming carbon dioxide upon reaction with the acid in the coagulation bath.

In some embodiments, the chemical blowing agent is a water soluble carbonate salt.

In some embodiments, the chemical blowing agent is sodium carbonate. The sodium carbonate may be added to the homogenous solution as a solid. In some embodiments, wherein the fibrous protein is wool, the fibrous protein: sodium carbonate ratio (w/w) is between about 4:1 and about 1:1, or about 2:1.

In some embodiments, wherein the fibrous protein is wool and the homogenous solution:sodium cellulose xanthate solution ratio (v/v) is about 1:1, the fibrous protein:sodium carbonate ratio (w/w) is about 1:1.

In some embodiments, wherein the alkaline solution comprises sodium hydroxide, the sodium carbonate is formed by reaction of $CO_2$ with the sodium hydroxide. The $CO_2$ may be added to the homogenous solution as a solid (dry ice). In some embodiments, wherein the fibrous protein is wool, the fibrous protein:dry ice ratio (w/w) is between about 2:1 and about 1:2, or about 1:1.

Upon mixing dry ice with the homogenous solution, the solution typically freezes. The solid mixture may then be thawed prior to immersion in the coagulation bath.

In some embodiments, the chemical blowing agent is sodium ethyl carbonate, which is commercially available, or can be prepared by reacting dry ice in ethanol and then reacting the mixture with NaOH. The sodium ethyl carbonate may then be added to the homogenous solution as a solution. In some embodiments, wherein the fibrous protein is wool, the homogenous solution comprises 20% wool, and the sodium ethyl carbonate solution is prepared by reacting dry ice (20 g) with ethanol (200 ml) and then adding 10% aqueous NaOH (100 ml) to the reaction mixture, the homogenous solution:sodium ethyl carbonate solution ratio (v/v) is between about 5:1 and about 1;1, or about 5:2.

The invention contemplates embodiments in which various of the modifications discussed above are combined, for example to form the proteinaceous material as a fibre-reinforced foam.

In some embodiments, the present invention provides a process for preparing proteinaceous fibres comprising:
(a) immersing wool in an alkaline solution;
(b) removing excess alkaline solution from the wool;
(c) ageing the mixture of wool and alkaline solution to form a homogenous solution; and (d) wet spinning the solution obtained in (c) to form the proteinaceous fibres.

In some embodiments, the present invention provides a process for preparing proteinaceous fibres comprising:
(a) immersing wool in an alkaline solution selected from aqueous NaOH, ethanolic sodium ethoxide, and ethanolic NaOH;
(b) removing excess alkaline solution from the wool;
(c) ageing the mixture of wool and alkaline solution to form a homogenous solution; and
(d) wet spinning the solution obtained in (c) to form the proteinaceous fibres.

In some embodiments, the present invention provides a process for preparing proteinaceous fibres comprising:
(a) immersing wool in an alkaline solution selected from aqueous NaOH, ethanolic sodium ethoxide and ethanolic sodium hydroxide;
(b) pressing the wool to remove excess alkaline solution;
(c) ageing the mixture of wool and alkaline solution for between about 15 minutes and about 180 minutes to form a homogenous solution; and
(d) wet spinning the solution obtained in (c) to form the proteinaceous fibres.

In some embodiments, the present invention provides a process for preparing proteinaceous fibres comprising:
(a) immersing wool in an alkaline solution selected from aqueous NaOH, ethanolic sodium ethoxide and ethanolic NaOH;
(b) pressing the wool to remove excess alkaline solution;
(c) ageing the mixture of wool and alkaline solution for between about 15 minutes and about 180 minutes to form a homogenous solution; and
(d) wet spinning the solution obtained in (c) by extrusion into a coagulation bath comprising an aqueous solution of sulfuric acid, sodium sulfate and zinc sulfate to form the proteinaceous fibres.

In some embodiments, the present invention provides a process for preparing proteinaceous fibres comprising:
(a) immersing wool in an alkaline solution selected from 10% aqueous NaOH, 20% ethanolic sodium ethoxide and 20% ethanolic NaOH;
(b) pressing the wool to remove excess alkaline solution;
(c) ageing the mixture of wool and alkaline solution for between about 90 minutes and about 180 minutes to form a homogenous solution; and
(d) wet spinning the solution obtained in (c) by extrusion into a coagulation bath comprising an aqueous solution of sulfuric acid, sodium sulfate and zinc sulfate to form the proteinaceous fibres.

In some embodiments, the present invention provides a process for preparing proteinaceous fibres comprising:
(a) immersing wool in an alkaline solution that is aqueous NaOH;
(b) removing excess alkaline solution from the wool;
(c) ageing the mixture of wool and alkaline solution to form a homogenous solution; and
(d) wet spinning the solution obtained in (c) to form the proteinaceous fibres.

In some embodiments, the present invention provides a process for preparing proteinaceous fibres comprising:
(a) immersing wool in an alkaline solution that is ethanolic sodium ethoxide;
(b) removing excess alkaline solution from the wool;
(c) ageing the mixture of wool and alkaline solution to form a homogenous solution; and
(d) wet spinning the solution obtained in (c) to form the proteinaceous fibres.

In some embodiments, the present invention provides a process for preparing proteinaceous fibres comprising:
(a) immersing wool in an alkaline solution that is ethanolic sodium hydroxide;
(b) removing excess alkaline solution from the wool;
(c) ageing the mixture of wool and alkaline solution to form a homogenous solution; and
(d) wet spinning the solution obtained in (c) to form the proteinaceous fibres.

In some embodiments, the present invention provides a process for preparing proteinaceous fibres comprising:
(a) immersing wool in an alkaline solution that is 10% aqueous NaOH;
(b) pressing the wool to remove excess alkaline solution;
(c) ageing the mixture of wool and alkaline solution for between about 90 minutes and about 150 minutes to form a homogenous solution; and
(d) wet spinning the solution obtained in (c) by extrusion into a coagulation bath comprising an aqueous solution of sulfuric acid, sodium sulfate and zinc sulfate to form the proteinaceous fibres.

In some embodiments, the present invention provides a process for preparing proteinaceous fibres comprising:
(a) immersing wool in an alkaline solution that is 20% ethanolic sodium ethoxide;
(b) pressing the wool to remove excess alkaline solution;
(c) ageing the mixture of wool and alkaline solution for about 180 minutes to form a homogenous solution; and
(d) wet spinning the solution obtained in (c) by extrusion into a coagulation bath comprising an aqueous solution of sulfuric acid, sodium sulfate and zinc sulfate to form the proteinaceous fibres.

In some embodiments, the present invention provides a process for preparing proteinaceous fibres comprising:
(a) immersing wool in an alkaline solution that is 20% ethanolic NaOH;
(b) pressing the wool to remove excess alkaline solution;
(c) ageing the mixture of wool and alkaline solution for about 180 minutes to form a homogenous solution; and
(d) wet spinning the solution obtained in (c) by extrusion into a coagulation bath comprising an aqueous solution of sulfuric acid, sodium sulfate and zinc sulfate to form the proteinaceous fibres.

In some embodiments, the present invention provides a process for preparing proteinaceous fibres comprising:
immersing wool in an alkaline solution;
ageing the mixture of wool and alkaline solution to form a homogenous solution; and wet spinning the homogenous solution to form the proteinaceous fibres.

In some embodiments, the present invention provides a process for preparing proteinaceous fibres comprising:
immersing wool in aqueous NaOH;
ageing the mixture of wool and alkaline solution to form a homogenous solution; and
wet spinning the homogenous solution to form the proteinaceous fibres.

In some embodiments, the present invention provides a process for preparing proteinaceous fibres comprising:
immersing wool in 10% aqueous NaOH;
ageing the mixture of wool and 10% aqueous NaOH for between about 45 minutes and about 60 minutes to form a homogenous solution; and
wet spinning the homogenous solution by extrusion into a coagulation bath comprising an aqueous solution of sulfuric acid, sodium sulfate and zinc sulfate to form the proteinaceous fibres.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution;
casting the homogenous solution into a mould; and
coagulating the homogenous solution by immersion into an acidic coagulation bath to form the proteinaceous material.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution;
casting the homogenous solution into a mould;
coagulating the homogenous solution by immersion into an acidic coagulation bath to form the proteinaceous material; and
immersing the proteinaceous material in an aqueous formaldehyde solution.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution; and
coagulating the homogenous solution by immersion into a coagulation bath comprising an acyl halide or acid anhydride to form the proteinaceous material.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution;
adding urea to the homogenous solution; and
coagulating the homogenous solution by immersion into an acidic coagulation bath to form the proteinaceous material.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution;
adding urea to the homogenous solution;
casting the homogenous solution onto a substrate; and
coagulating the homogenous solution by immersion into an acidic coagulation bath to form the proteinaceous material.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution;
adding a blowing agent to the homogenous solution; and
coagulating the homogenous solution by immersion into an acidic coagulation bath to form the proteinaceous material.

In some embodiments, the present invention provides a process for preparing a proteinaceous material comprising:
immersing wool in 10% aqueous NaOH;

ageing the mixture of wool and 10% aqueous NaOH for between about 45 minutes and about 60 minutes to form a homogenous solution;
adding a blowing agent to the homogenous solution;
coagulating the homogenous solution by immersion into an acidic coagulation bath to form the proteinaceous material; and
immersing the proteinaceous material in an aqueous formaldehyde solution.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution;
adding a carboxylic acid or salt thereof to the homogenous solution; and
coagulating the homogenous solution by immersion into an acidic coagulation bath to form the proteinaceous material.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution;
adding a silicate or phosphate salt to the homogenous solution; and
coagulating the homogenous solution by immersion into an acidic coagulation bath to form the proteinaceous material.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution;
adding a solution of a polymer precursor to the homogenous solution; and
coagulating the homogenous solution by immersion into an acidic coagulation bath to form the proteinaceous material.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution;
adding a solution of a polymer precursor and a blowing agent to the homogenous solution; and
coagulating the homogenous solution by immersion into an acidic coagulation bath to form the proteinaceous material.

In some embodiments, the present invention provides a process for preparing a proteinaceous material comprising:
immersing wool in 10% aqueous NaOH;
ageing the mixture of wool and 10% aqueous NaOH for between about 45 minutes and about 60 minutes to form a homogenous solution;
adding a solution of sodium cellulose xanthate to the homogenous solution; and
coagulating the homogenous solution by immersion into an acidic coagulation bath to form the proteinaceous material.

In some embodiments, the present invention provides a process for preparing a proteinaceous material comprising:
immersing wool in 10% aqueous NaOH;

ageing the mixture of wool and 10% aqueous NaOH for between about 45 minutes and about 60 minutes to form a homogenous solution;

adding a solution of sodium cellulose xanthate and a blowing agent to the homogenous solution; and coagulating the homogenous solution by immersion into an acidic coagulation bath to form the proteinaceous material.

In some embodiments, the present invention provides a process for preparing a proteinaceous material comprising:

immersing wool in 10% aqueous NaOH;

ageing the mixture of wool and 10% aqueous NaOH for between about 45 minutes and about 60 minutes to form a homogenous solution;

adding a solution of a polymer to the homogenous solution; and coagulating the homogenous solution by immersion into an acidic coagulation bath to form the proteinaceous material.

In some embodiments, the present invention provides a process for preparing a proteinaceous material comprising:

immersing wool in 10% aqueous NaOH;

ageing the mixture of wool and 10% aqueous NaOH for between about 45 minutes and about 60 minutes to form a homogenous solution;

adding a solution of a polymer and a blowing agent to the homogenous solution; and coagulating the homogenous solution by immersion into an acidic coagulation bath to form the proteinaceous material.

In some embodiments, the present invention provides a process for preparing a proteinaceous material comprising:

immersing wool in 10% aqueous NaOH;

ageing the mixture of wool and 10% aqueous NaOH for between about 45 minutes and about 60 minutes to form a homogenous solution;

adding a solution of polystyrene to the homogenous solution; and coagulating the homogenous solution by immersion into an acidic coagulation bath to form the proteinaceous material.

In some embodiments, the present invention provides a process for preparing a proteinaceous material comprising:

immersing wool in 10% aqueous NaOH;

ageing the mixture of wool and 10% aqueous NaOH for between about 45 minutes and about 60 minutes to form a homogenous solution;

adding a solution of polystyrene and a blowing agent to the homogenous solution; and coagulating the homogenous solution by immersion into an acidic coagulation bath to form the proteinaceous material.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

The following non-limiting examples are provided to illustrate the present invention and in no way limit the scope thereof.

EXAMPLES

Example 1

Raw wool suitable for use in the carpet industry was scoured with detergents, such as alkylphenol ethoxylates (APEOs) or fatty alcohol ethoxylates, and 10% aqueous sodium carbonate.

Scoured wool (1 gram) was placed into a sieve and immersed into 20 ml of 10% aqueous NaOH for 45-60 seconds with stirring. The sieve was then removed from the NaOH solution.

The wool was then pressed to remove the excess NaOH solution, using a press suitable for removing excess NaOH solution from alkali-cellulose in the viscose process. The resulting moist wool weighed 2-2.3 grams.

The moist wool was aged for about 45 minutes to form a paste. After 90 minutes ageing, a homogenous solution having the consistency of viscous honey was formed.

If the resulting homogenous solution could not be processed within a further hour, it was frozen and then thawed prior to further processing.

The viscosity of the resulting homogenous solution was adjusted with 2% aqueous NaOH, if necessary, and the solution filtered. The solution was then transferred to a syringe and spun using a conventional wet spinning machine typically used for viscose. Accordingly, the solution was forced from the syringe through a spinneret into a coagulation bath.

The coagulation bath comprised 110 g/l sulfuric acid, 350 g/l sodium sulfate and 10 g/l zinc sulfate.

After coagulation, the resulting fibres were collected and then treated with 20% aqueous sodium carbonate. The fibres were then air dried and wound onto a bobbin.

Example 2

Scoured wool (1 grain) was placed into a sieve and immersed into 40 ml of 20% ethanolic sodium ethoxide, prepared by dissolving solid sodium ethoxide in ethanol, for 10-15 minutes with stirring. The sieve was then removed from the sodium ethoxide solution.

The wool was then pressed to remove the excess sodium ethoxide solution, using the press used in Example 1. The resulting moist wool weighed 1.88-2 grams.

The moist wool was aged for about 2 hours to form a paste. After 3 hours ageing, a homogenous solution having the consistency of viscous honey was formed.

The resulting homogenous solution was then wet spun as in Example 1.

Example 2a

The process of Example 2 was repeated using 40 ml of 20% ethanolic sodium hydroxide, which was prepared by dissolving sodium hydroxide (20 g) in ethanol (100 ml).

Example 3

Scoured and bleached wool (40 grams), obtained from a commercial scour, was immersed into 10% aqueous NaOH (200 ml) and the mixture stirred for 2 minutes. The mixture was then aged for 45 to 60 minutes to form a homogenous solution.

Example 3a

For wet spinning, the viscosity of the homogenous solution formed in Example 3 was adjusted by adding an equal volume of distilled water.

Example 4

Bleached wool (40 grams) was immersed into 200 ml of 10% aqueous NaOH and the mixture stirred for 2 minutes. The wool was then removed from the NaOH solution and then pressed to remove excess liquid.

The resulting moist wool weighed about 100 grams.

The moist wool was placed in a 200 ml beaker, which was then placed into a 1000 ml container. Water (100 ml) was then poured into the bottom of the container, and the container sealed. The container was then maintained at ambient temperature. The moist wool was aged for about 2 hours to form a paste and subsequently a homogenous solution.

The homogenous solution in the beaker was maintained in the sealed container. The homogenous solution maintained its viscosity for more than 2 days after which it could still be wet spun as in Example 1.

Example 5

A homogenous solution formed as in Example 3 was poured into a mould with a closed base to a depth of about 2 cm. The filled mould was then immersed into an acid bath comprising glacial acetic acid or 110 g/l sulfuric acid (as in Example 1) for about 5 to 6 hours to form a rigid plastic.

The filled mould was then removed from the acid bath and immersed into water for about an hour to remove residual acid, during which the rigid plastic was removed from the mould.

The rigid plastic was then hardened by immersion into 30% aqueous formaldehyde for about a day and then rinsed in water and air-dried.

Example 5a

A homogenous solution (50 ml) formed as in Example 3 was mixed with glass fibres (5 to 10 g).

The resulting mixture was then processed as in Example 5.

Example 6

A homogenous solution (50 ml) formed as in Example 3 was diluted with 50 ml water. Urea (10 g) was added and the mixture stirred. About 2 ml of the resulting mixture was then dripped onto a flat glass plate (15 cm×15 cm) to form a thin layer almost covering the entire surface, after which the glass plate was immersed into an acid bath comprising glacial acetic acid for between about 5 minutes and about 20 minutes.

The glass plate bearing the resulting film was then immersed into water for about 1 minute, after which the film was removed from the glass plate and air-dried. The film was of comparable thickness to paper.

Example 6a

A homogenous solution (50 ml) formed as in Example 3 was diluted with 50 ml water. PEG 6000 (20%, 20 ml) was added and the mixture stirred. About 2 ml of the resulting mixture was then dripped onto a flat glass plate (15 cm×15 cm) to form a thin layer almost covering the entire surface, after which the glass plate was immersed into an acid bath comprising glacial acetic acid for about 20 minutes.

The glass plate bearing the resulting film was then immersed into water for about 1 minute, after which the film was removed from the glass plate. The film was of comparable thickness to paper.

Example 7

The homogenous solution mixed with urea (as in Example 6) or PEG 6000 (as in Example 6a) was wet spun as in Example 1.

Example 8

A homogenous solution formed as in Example 3 was poured into an acid bath comprising glacial acetic acid or 110 g/l sulfuric acid (as in Example 1).

The resulting randomly shaped plastic was collected, rinsed with water and air-dried. The dried plastic was then ground in an electric coffee grinder to form a powder.

Example 9

A homogenous solution (50 ml) formed as in Example 3 was mixed with sodium carbonate (5 g).

The mixture was poured into a mould with a closed base. The filled mould was then immersed into an acid bath comprising glacial acetic acid or 110 g/l sulfuric acid (as in Example 1) for about 5 to 15 minutes to form a rigid foam.

The filled mould was then removed from the acid bath and immersed into water for about 15 minutes to remove residual acid, during which the rigid foam was removed from the mould, and the rigid foam then rinsed. The rigid foam was then air-dried.

Example 10

A homogenous solution (50 ml) formed as in Example 3 was mixed with dry ice (10 g).

The mixture was left to defrost at ambient temperature and was then poured into a mould with a closed base. The filled mould was then immersed into an acid bath comprising glacial acetic acid or 110 g/l sulfuric acid (as in Example 1) for about 5 to 15 minutes to form a rigid foam.

The filled mould was then removed from the acid bath and immersed into water for about 15 minutes to remove residual acid, during which the rigid foam was removed from the mould, and the rigid foam then rinsed. The rigid foam was then air-dried.

Example 11

A homogenous solution (50 ml) formed as in Example 3 was mixed with a solution of sodium ethyl carbonate (20 ml). The sodium ethyl carbonate solution was prepared by reacting dry ice (20 g) with ethanol (200 ml) and then adding 10% aqueous NaOH (100 ml) to the reaction mixture.

The mixture was poured into a mould with a closed base. The filled mould was then immersed into an acid bath comprising glacial acetic acid or 110 g/l sulfuric acid (as in Example 1) for about 5 to 15 minutes to form a rigid foam.

The filled mould was then removed from the acid bath and immersed into water for about 15 minutes to remove residual acid, during which the rigid foam was removed from the mould, and the rigid foam then rinsed. The rigid foam was then air-dried.

Example 12

Monosodium phthalate (5 g) was mixed with a homogenous solution (50 ml) formed as in Example 3.

The resulting mixture was then mixed with an equal volume of water and wet spun as in Example 1.

Alternatively, the resulting mixture was foamed with sodium carbonate (as in Example 9), dry ice (as in Example 10), or sodium ethyl carbonate solution (as in Example 11), optionally with the further addition of 5 g of urea to the resulting mixture prior to foaming.

Example 13

Sodium acetate (5 g) was dissolved in water (50 ml) and then mixed with a homogenous solution (50 ml) formed as in Example 3.

The resulting mixture was then wet spun as in Example 1.

Alternatively, a mixture of sodium acetate (5 g) and a homogenous solution (50 ml) formed as in Example 3 was foamed with sodium carbonate (as in Example 9), dry ice (as in Example 10), or sodium ethyl carbonate solution (as in Example 11), optionally with the further addition of 5 g of urea to the resulting mixture prior to foaming.

Example 14

Sodium metasilicate ($Na_2SiO_3$, 5 g) was mixed with a homogenous solution (50 ml) formed as in Example 3.

The resulting mixture was then mixed with an equal volume of water and wet spun as in Example 1.

Example 14a

The process of Example 14 was repeated using sodium orthosilicate ($Na_4SiO_4$, 5 g).

Alternatively, the resulting mixture of the homogenous solution and sodium orthosilicate was foamed with sodium carbonate (as in Example 9), dry ice (as in Example 10), or sodium ethyl carbonate solution (as in Example 11), optionally with the further addition of 5 g of urea to the resulting mixture prior to foaming.

Example 15

Sodium terephthalate (5 g) was mixed with a homogenous solution (50 ml) formed as in Example 3.

The resulting mixture was then mixed with an equal volume of water and wet spun as in Example 1.

Alternatively, the resulting mixture was foamed with sodium carbonate (as in Example 9), dry ice (as in Example 10), or sodium ethyl carbonate solution (as in Example 11), optionally with the further addition of 5 g of urea to the resulting mixture prior to foaming.

Example 15a

The process of Example 15 was repeated using sodium terephthalate. The sodium terephthalate was obtained by saponifying PET (10 g) with 20% aqueous NaOH (200 ml) for at least a week.

Example 16

Terephthalic acid (5 g) was mixed with a homogenous solution (50 ml) formed as in Example 3.

The resulting mixture was then mixed with an equal volume of water and wet spun as in Example 1.

Alternatively, the resulting mixture was foamed with sodium carbonate (as in Example 9), dry ice (as in Example 10), or sodium ethyl carbonate solution (as in Example 11), optionally with the further addition of 5 g of urea to the resulting mixture prior to foaming.

Example 16a

Isophthalic acid (5 g) was mixed with a homogenous solution (50 ml) formed as in Example 3.

The resulting mixture was then mixed with an equal volume of water and wet spun as in Example 1.

Example 17

Trisodium benzene-1,3,5-tricarboxylate (5 g) was mixed with a homogenous solution (50 ml) formed as in Example 3.

The resulting mixture was then mixed with an equal volume of water and wet spun as in Example 1.

Alternatively, the resulting mixture was foamed with sodium carbonate (as in Example 9), dry ice (as in Example 10), or sodium ethyl carbonate solution (as in Example 11), optionally with the further addition of 5 g of urea to the resulting mixture prior to foaming.

Example 17a

The process of Example 17 was repeated using disodium benzene-1,3,5-tricarboxylate (5 g).

Example 17b

The process of Example 17 was repeated using monosodium benzene-1,3,5-tricarboxylate (5 g).

Example 18

Benzene-1,3,5-tricarboxylic acid (10-20 g) was mixed with a homogenous solution (200 ml) formed as in Example 3.

The resulting mixture was then mixed with an equal volume of water and wet spun as in Example 1.

Alternatively, the resulting mixture was foamed with sodium carbonate (as in Example 9), dry ice (as in Example 10), or sodium ethyl carbonate solution (as in Example 11), optionally with the further addition of 5 g of urea to the resulting mixture prior to foaming.

Example 19

Oxalic acid (10 g) was mixed with a homogenous solution (50 ml) formed as in Example 3. An exothermic reaction ensued, after which a solid product was obtained.

Example 20

A diluted homogenous solution formed as in Example 3a was wet spun as in Example 1, using a coagulation bath comprising 50 g/l oxalic acid, 110 g/l sulfuric acid, 350 g/l sodium sulfate and 10 g/l zinc sulfate.

Example 21

A diluted homogenous solution (10 ml) formed as in Example 3a was wet spun as in Example 1, using 200 ml benzoyl chloride as the coagulation bath.

Example 22

A diluted homogenous solution (10 ml) formed as in Example 3a was wet spun as in Example 1, using 200 ml acetyl chloride as the coagulation bath.

Example 23

A diluted homogenous solution (10 ml) formed as in Example 3a was wet spun as in Example 1, using 100 ml of 10% ethanolic terephathaloyl dichloride as the coagulation bath. The coagulation bath was prepared by dissolving the terephathaloyl dichloride in ethanol with heating.

Example 24

A diluted homogenous solution (10 ml) formed as in Example 3a was wet spun as in Example 1, using 200 ml acetic anhydride as the coagulation bath.

Example 25

A homogenous solution (50 ml) formed as in Example 3 was mixed with a 20% solution of sodium cellulose xanthate in 20% aqueous NaOH (50 ml).

The resulting mixture was then wet spun as in Example 1.

Example 26

70% aqueous ethanol (10 ml) was added to a homogenous solution (50 ml) formed as in Example 3, a 20% solution of polystyrene in ethyl acetate (50 ml), prepared by dissolving polystyrene foam (10 g) in the solvent, was then slowly added with stirring.

The resulting mixture was then wet spun as in Example 1.

Example 27

A homogenous solution (50 ml) formed as in Example 3 was mixed with a 20% solution of sodium cellulose xanthate in 20% aqueous NaOH (50 ml). Sodium carbonate (10 g) was added.

The resulting mixture was poured into a mould with a closed base. The filled mould was then immersed into an acid bath comprising glacial acetic acid or 110 g/l sulfuric acid (as in Example 1) for about 15 minutes to form a foam.

The filled mould was then removed from the acid bath and immersed into water for about 15 minutes to remove residual acid, during which the foam was removed from the mould, and the foam then rinsed. The foam was then air-dried.

It is not the intention to limit the scope of the invention to the abovementioned examples only. As would be appreciated by a skilled person in the art, many variations are possible without departing from the scope of the invention as set out in the accompanying claims.

INDUSTRIAL APPLICATION

It will be appreciated from the discussion above that the present invention provides a process for the production of proteinaceous materials from fibrous protein. The proteinaceous materials can be produced in the form of, for example, fibres, films, sheets, coatings, particles, shapes, foams or composites, the dimensions of which are independent of the dimensions of the fibrous protein starting material.

Those persons skilled in the art will understand that the above description is provided by way of illustration only and that the invention is not limited thereto.

The invention claimed is:

1. A process for preparing a proteinaceous material comprising:
    (a) contacting fibrous protein comprising keratin with an alkaline solution selected from the group consisting of: an aqueous solution of an alkali metal hydroxide, wherein the concentration of the alkali metal hydroxide is between about 10% and about 20%; alcoholic alkali metal alkoxide, wherein the concentration of the alkali metal alkoxide is between about 5% and about 30%; and alcoholic alkali metal hydroxide, wherein the concentration of the alkali metal hydroxide is between about 5% and about 30%;
    (b) removing excess alkaline solution from the fibrous protein;
    (c) ageing the mixture of fibrous protein and alkaline solution to form a homogenous solution having a viscosity of about 5,000 cP to about 20,000 cP; and
    (d) coagulating the solution obtained in (c) to form the proteinaceous material.

2. A process as claimed in claim 1, wherein the fibrous protein comprises wool.

3. A process as claimed in claim 1, wherein the alkaline solution is aqueous NaOH.

4. A process as claimed in claim 3, wherein the concentration of NaOH is about 10%.

5. A process as claimed in claim 1, wherein the contacting and ageing steps are performed at ambient temperature.

6. A process as claimed in claim 2, wherein after removing excess alkaline solution the mixture of wool and alkaline solution comprises between about 50% and about 200% alkaline solution by the initial weight of the wool.

7. A process as claimed in claim 2, wherein the ratio of wool weight (in grams) to alkaline solution volume (in ml) is between about 1:2 and about 1:10.

8. A process as claimed in claim 2, wherein the wool is contacted with the alkaline solution for up to about 5 minutes.

9. A process as claimed in claim 2, wherein the mixture of wool and alkaline solution is aged for between about 15 minutes and about 180 minutes.

10. A process as claimed in claim 2, wherein the wool and the alkaline solution are contacted and aged for between about 15 minutes and about 180 minutes.

11. A process as claimed in claim 1, further comprising adding one or more plasticiser to the homogenous solution prior to coagulation.

12. A process as claimed in claim 1, further comprising adding urea or a functional analogue thereof to the homogenous solution prior to coagulation.

13. A process as claimed in claim 1, further comprising combining the homogenous solution with one or more other polymer precursor prior to coagulation.

14. A process as claimed in claim 1, further comprising combining the homogenous solution with one or more polymer prior to coagulation.

15. A process as claimed in claim 1, wherein the homogenous solution is coagulated by treating the solution with a liquid coagulant.

16. A process as claimed in claim 1, wherein the homogenous solution is coagulated by immersion in a coagulation bath.

17. A process as claimed in claim 1, further comprising adding a blowing agent to the homogenous solution prior to coagulation.

18. A process as claimed in claim 1, wherein the proteinaceous material comprises a fibre, film, sheet, coating, particle, shape, foam or composite.

* * * * *